United States Patent [19]

Conrad

[11] Patent Number: 5,138,889

[45] Date of Patent: Aug. 18, 1992

[54] HAND HELD EXPLOSIVES DETECTION SYSTEM

[75] Inventor: Frank J. Conrad, Albuquerque, N. Mex.

[73] Assignee: The United States of America as represented by the United States Department of Energy, Washington, D.C.

[21] Appl. No.: 596,104

[22] Filed: Oct. 11, 1990

[51] Int. Cl.⁵ ............................................. G01N 1/22
[52] U.S. Cl. .................... 73/863.12; 73/864.81
[58] Field of Search ........... 73/863.11, 863.12, 863.21, 73/864.21, 864.81, 864.83, 864.34, 864.73, 23.41

[56] References Cited

U.S. PATENT DOCUMENTS

| | | | |
|---|---|---|---|
| 3,998,101 | 12/1976 | Bradshaw et al. | 73/421.5 R |
| 4,003,260 | 1/1977 | Catoul | 73/423 R |
| 4,170,901 | 10/1979 | Conkle et al. | 73/863.12 |
| 4,344,917 | 8/1982 | Schorno | 73/863.12 |
| 4,718,268 | 1/1988 | Reid et al. | 73/23 |
| 4,732,046 | 3/1988 | Lawrence et al. | 73/863.12 |
| 4,818,870 | 4/1989 | Griffiths | 250/288 |
| 4,820,920 | 4/1989 | Bather | 250/282 |

OTHER PUBLICATIONS

L. Lanning et al., "Electrically Heated Cold Trap Inlet System for Computer-Controlled High-Speed Gas Chromatography", *Analytical Chemistry*, vol. 60, No. 18, Sep. 15, 1988, pp. 1994–1996.
Advertisements from Sensing Technology, Inc. ("Scantex Jr., Explosive Detector"), from ITI Security Advanced Bomb and Weapon Detection System), and From Graseby Dynamics Ltd. (Graseby Ionics, Explosives Detector PD5).

*Primary Examiner*—Robert Raevis
*Attorney, Agent, or Firm*—Anne D. Daniel; James H. Chaffin; William R. Moser

[57] ABSTRACT

The present invention is directed to a sensitive hand-held explosives detection device capable of detecting the presence of extremely low quantities of high explosives molecules, and which is applicable to sampling vapors from personnel, baggage, cargo, etc., as part of an explosives detection system.

3 Claims, 2 Drawing Sheets

HAND HELD EXPLOSIVES DETECTION SYSTEM

BACKGROUND OF THE INVENTION

1. Field of the Invention

The present invention relates to novel vapor sampler apparatus useful in preparing sensitive, hand-held explosives detector systems. In particular, it addresses the problem of sampling explosives vapors, i.e., obtaining the vapor sample and transporting it to the detector in toto, without significant loss. The sampler apparatus are useful in sampling for any electronegative explosive vapor, including those such as plastic explosives, which have very low vapor pressures.

2. Description of Related Art

A major problem associated with the detection of explosives in airports, nuclear facilities, secure areas, and elsewhere is that the molecules which are available for detection are available in only minute quantities. For example, in the case of the lower vapor pressure explosives, there are only about $6 \times 10^{-14}$ gm of explosives molecules per cubic centimeter (cc) of air at room temperature and pressure. This is approximately 1 million times less than the amount of pollution regularly found in a cc of air on a good day. Thus, the exceedingly low quantity of explosives molecules available for detection indicates the need for a highly sensitive detector system.

For many years, Electron Capture Detectors (ECD) have been employed commercially in explosives detection systems, and have been thought to be the detector of choice in such systems. An ECD is normally used in line in an explosives detection system after the materials present in a test sample have been separated on a gas chromatography column. Such a detection system is generally denoted as a GC-ECD System. While the sensitivity number for an ECD detector has recently been calculated to be $8 \times 10^{-15}$ gm of explosives/cc, most commercial GC-ECD detection devices cannot consistently detect trinitrotoluene (TNT) vapor at $6 \times 10^{-11}$ gm of explosives/cc. One possible reason for the loss of sensitivity encountered when using a GC-ECD detection system is that explosives molecules possess adhesive properties, sticking to every metal, plastic, ceramic, etc. with which they have been tested. It is this property that excludes the commercial GC-ECD devices from detecting all the explosives of interest since many of the explosives molecules in a test sample stick to surfaces of the instrument which precede the ECD itself, and thus never reach the detector.

The results of tests on a variety of commercially available explosives detectors, involving evaluation of their sensitivity to a variety of explosives, identification of false alarm agents, and general performance and maintenance characteristics, have revealed that most explosives detectors have difficulty in detecting, or are not applicable to, the detection of RDX (cyclonite) or PETN (pentaerythritol-tetranitrate) plastic explosives, or any other electronegative explosives which have vapor pressures in the low range of these materials (i.e., about one part per trillion).

Bradshaw et al., in U.S. Pat. No. 3,998,101, disclose a device for sampling non-hermetically sealed containers, but do not specify the detector employed. With the disclosed system, when the sample is taken, it is removed and transported to the detector. The system is not "hand held", and in addition, the power requirements for the sample portion of the device are quite large.

Reid et al., in U.S. Pat. No. 4,718,268, disclose an explosives detection device wherein the sample is obtained and subsequently transported to the detector. The detector is a mass spectrometer which weighs several hundred pounds, and thus is not "hand held". This system is designed for sampling large volumes.

Griffiths, in U.S. Pat. No. 4,818,870, discloses an explosives detection device which is a sampling probe only, and not a sampling/detection system. The size of the probe described therein indicates that it is not intended as a "hand held" device. Bather, in U.S. Pat. No. 4,820,920, discloses an explosives detection system which is neither "hand held" nor "portable".

Finally, Lanning et al (*Anal. Chem.* (1988) 60: 1994-1996) have described a detector device which differs from that of the present invention in that the "sampler" does not move into the external environment to collect the sample. Failure to extend the sampler out into the area to be screened accounts for the inability of commercial explosives detectors to detect all of the explosives present in a sampling environment.

SUMMARY OF THE INVENTION

Therefore, it is an object of the present invention to provide a sensitive hand held explosives sampler apparatus, which is useful in preparing a portable explosives detection system capable of detecting extremely low levels of explosives vapors, including electronegative explosives vapors such as those of plastic explosives, which have very low vapor pressure. As compared to presently commercially available devices, it is an object of the present invention that such a system possesses the advantage of being usable for on site detection as opposed to sampling with remote detection. It is a further object of the present invention that the sampler apparatus be capable of sampling small volumes, including personnel, baggage, cargo, etc., and that it possesses only modest power requirements, so that it can operate on a portable power source, such as batteries.

The foregoing objects and others are accomplished in accordance with the present invention by providing a device which eliminates all the cold surfaces in a sampler apparatus upon which explosives vapor molecules might collect before they reach the sampler's trap (sample collector element), and thereafter facilitates rapid, quantitative transfer of the collected sample to an explosives detector. This is accomplished by providing means which allow at least a portion of the sampler's trap (sample collector element) to travel into the exterior sampling environment, wherein the collecting of a sample occurs. Thereafter, the sampler's trap returns into the sampler apparatus, wherein the sample is heated within the sample collector element and cleaned rapidly so as to transfer the collected sample from the collector element through a GC Column to a suitable detector. The gas chromatographic column resolves the sample vapor into its component constituents through heated lines so that no sample is lost via adsorption onto the walls. This sample apparatus can detect explosives at a vapor pressure of six parts per trillion, v/v, at room temperature and pressure.

BRIEF DESCRIPTION OF THE DRAWINGS

The above and other objects, features, and advantages of the present invention will be better understood from the following detailed descriptions taken in conjunction with the accompanying drawings, all of which are given by way of illustration only, and are not limitative of the present invention, in which.

DETAILED DESCRIPTION OF THE INVENTION

Figure 1:
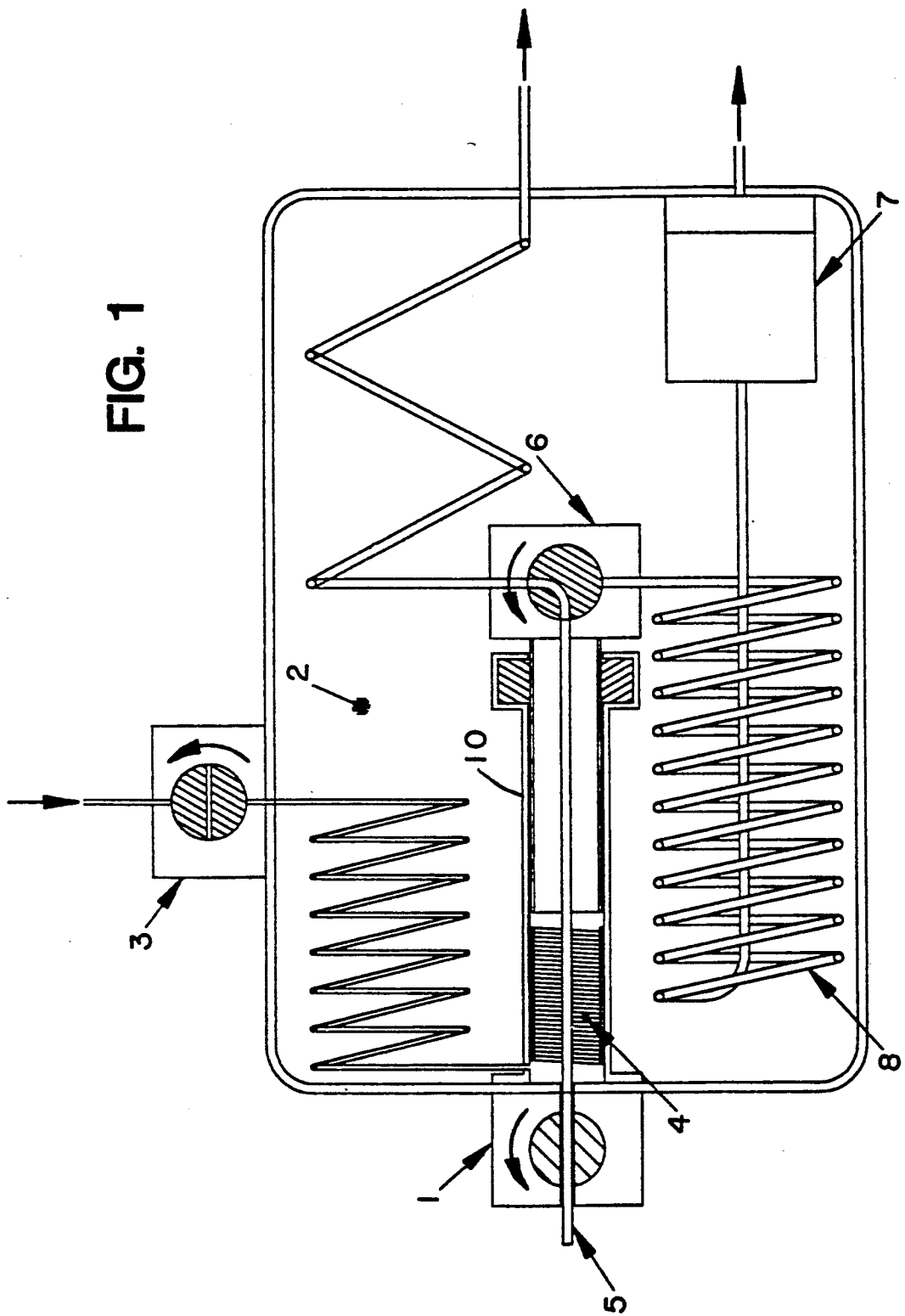
FIG. 1 is a diagram of an explosives sensor apparatus according to the present invention in the sampling position.

The following detailed description of the invention is provided to aid those skilled in the art in practicing the present invention. Even so, the following detailed description of the invention should not be construed to unduly limit the present invention, as modifications and variations in the embodiments herein discussed may be made by those of ordinary skill in the art without departing from the spirit or scope of the present inventive discovery.

The present invention is concerned with providing new explosives sampling apparatus which facilitate the detection of ultra low quantities of explosives molecules occurring in an air sample via the transfer of such molecules to an explosives detector, without significant loss thereof, after sampling. The present inventive explosives sampling apparatus can perform this function because of their novel design and the ability of such a design to advantageously exploit the adhesive properties of explosive molecules as an aid in their detection.

While many different embodiments of explosives sampler apparatus are encompassed by the present invention, it is noted that such apparatus still have many characteristics in common. For example, an explosives sampler apparatus according to the present invention could be characterized as follows:

An explosives sampler apparatus, having a sampler collector element existing in a protected environment;

means connected to said element for heating at least a portion thereof;

means connected to said element for reversibly extending at least a portion of the element directly into an intended sampling environment;

means connected to said element for sampling the intended sampling environment, when at least a portion of the element is extended into the intended sampling environment;

means connected to said element for transferring a collected sample from said element to an explosives detector through a gas chromatographic column.

In order to aid those desiring to utilize the present inventive devices, the following discussion relating to suitable sampler collector elements, and means connected thereto for preparing sampler apparatus according to the present invention, are provided.

Since explosives molecules which are to be detected usually possess adhesive properties, any sampler collector element utilized in the sample apparatus of the present invention should be capable of exploiting this property. Thus, sampler collector elements employed in the apparatus of the present invention should be comprised of materials to which explosives molecules may easily, and preferably, adhere. Exemplary of such materials are siliceous materials as well as certain metals. Exemplary of such siliceous materials are quartz, fused silica, and glass. Exemplary of suitable metals are gold, nickel, and stainless steel. Regarding physical configurations for sample collector elements in the apparatus according to the present invention, it is noted that a tubular configuration is thought preferred, but not limiting, to the present invention. It is specifically noted that other configurations may be employed without departing from the spirit or scope of the present invention. Even so, a tubular configuration for collecting elements in the apparatus of the present invention allows for what is believed to be a simplified design which allows for both ease of manufacture and ease of replacement in the apparatus of the present invention. Moreover, the use of a tubular design allows for the effective use of both forced air and vacuum means to both collect explosive molecules on the collector element, and to transport said molecules from the element to a suitable explosives detector. Even so, it is fully envisioned that other shapes of explosive sampler elements may be advantageously utilized in the present invention. For example, it is envisioned that either a solid needlelike configuration or a platelike configuration would be useful in the present invention. It is noted that in the specific embodiment of the present invention discussed below and shown in FIGS. 1 and 2, the collector element possesses a tubular configuration.

Figure 2:
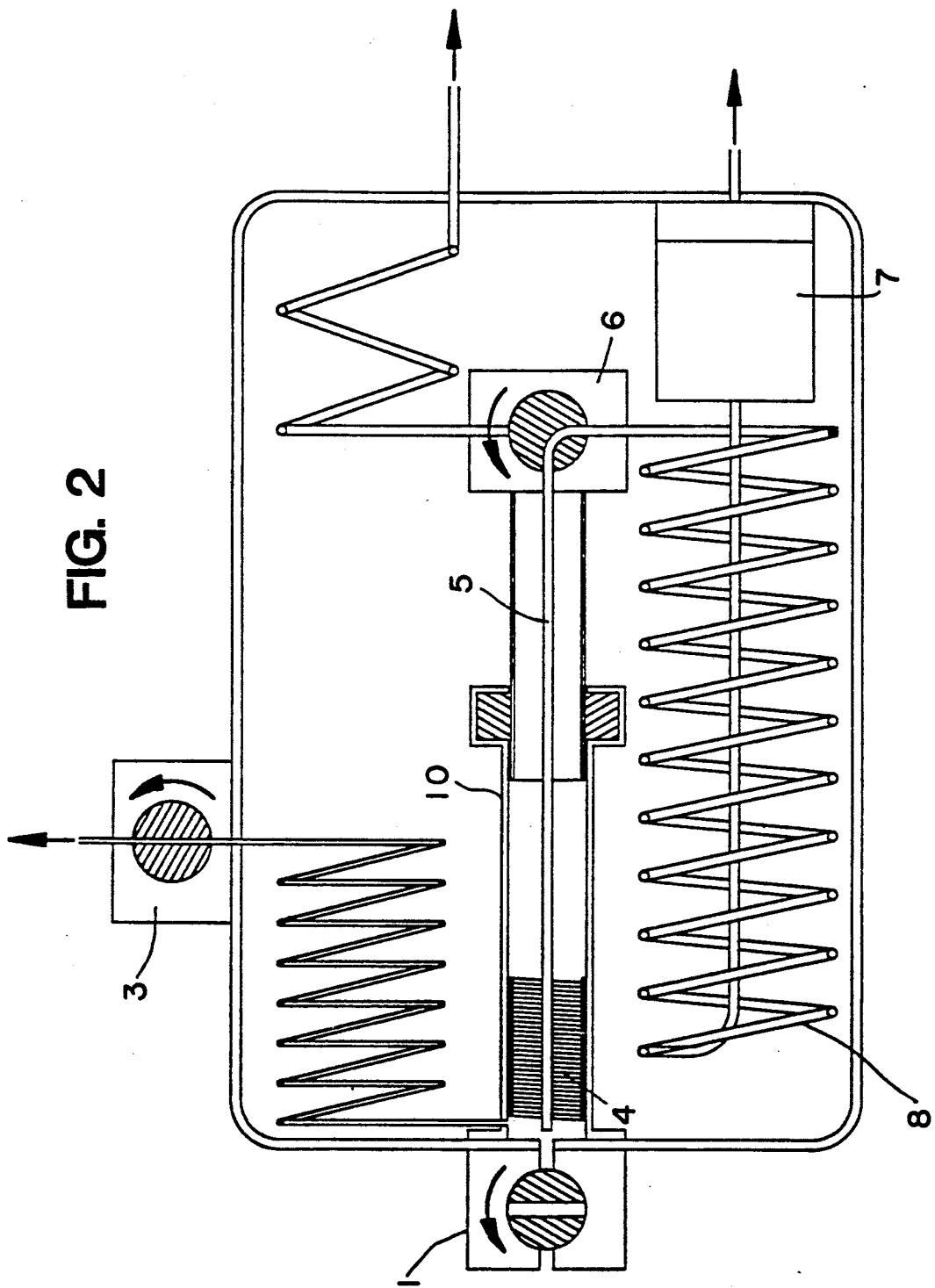
FIG. 2 is a diagram of an explosives sensor apparatus according to the present invention in the sample detection position.

Regarding means encompassed herein for heating at least a portion of the element, it is noted that several different means may be utilized, and that such means may be utilized separately or in combination. For example, as shown in FIGS. 1 and 2, a heating oven may be used in conjunction with an extra heating wire to heat a collector element found in the sampler apparatus according to the present invention. It is noted that heating of the element occurs so as to allow for both cleaning of the element prior to or after sampling, and for transfer of molecules collected on the element during sampling. In this regard, it is noted that even though the explosive molecules possess adhesive properties, which advantageously allow the same to deposit on the surface of the collector elements found in the apparatus of the present invention, such molecules may be volatilized off the surface of such elements by heating.

In the explosives sample apparatus of the present invention, means exist for reversibly extending at least a portion of the collector element referred to above directly into an intended sampling environment. Such may be achieved as shown in FIG. 1; however, the same is not limited to the present invention, and other acceptable extending means should be readily understood by those of ordinary skill in the art, and the same are encompassed hereby.

It is noted that the provision of extending means in the apparatus according to the present invention is most advantageous since it allows for the sampling of ultra small quantities of explosives molecules occurring in an explosives vapor. By extending a portion of the collector sampler into the intended sampling environment, the present inventor has effectively eliminated all surfaces to which explosives molecules might adhere before reaching the sampler element. Additionally, by extending an end of the sampling element into the intended environment, cooling of the extended portion of the element is facilitated, so that molecules can easily stick thereto. It is noted that in the instance of an apparatus such as that shown in FIG. 1, wherein the sampling element has a low mass, cooling of the extended portion thereof occurs rapidly. It is for this reason that sampler collector elements occurring in the explosive sampler apparatus of the present invention preferably possess a low mass. Additionally, such preferred elements, due to their low masses, can be heated rapidly to high temperatures whereby molecules collected on the surfaces thereof can be removed after volatilization by forced air means. Such a configuration is outlined in the apparatus shown in FIG. 1.

Once a portion of the sampling element found in the apparatus according to the present invention is extended into an intended sampling environment, sampling of the environment must occur. Means for providing such sampling can of course be varied. Even so, it is thought useful in the present invention if vacuum means are utilized to perform such sampling. For instance, in the case where the sampling element has a tubular configuration, a vacuum can be attached to an end opposite the portion of the element extended into the intended sampling environment, and air from the sampling environment can be drawn through the element. In such a manner, explosives molecules are drawn through the element along with air, and advantageously, if explosives molecules are present, the same should stick to surfaces of the element. In this regard, it is noted that by drawing air through the element, a slight cooling of the element can also be achieved, whereby even previously heated surfaces may be rapidly cooled and advantageously used to contact explosives molecules.

Sampling times utilizing the apparatus according to the present invention are not unduly long. For example, a sampling time of about 0.5 seconds is thought adequate to sample a cloud of explosives molecules surrounding a bomb, while one to several minutes may be required to properly search a car, room, building, etc. for an explosive device. Normally, however, sampling for only a few seconds is sufficient for probing a limited environment for the presence of explosives molecules. With regard to air sample volumes, a sampling volume of about one to two cubic centimeters is thought sufficient for determining whether explosives molecules exist in the sampling environment as a vapor cloud.

It is additionally noted that a tubular configuration for a sampler collector element is thought most advantageous in the present invention, since it seems to more readily allow for preconcentration of explosives molecules found in the sampled environment. More specifically, by utilizing a collector element having a tubular configuration and connecting thereto appropriate vacuum means, one may collect explosives molecules found in a relatively large volume of sample space onto a relatively small surface of a collector element. Thereafter, such a concentrated presence of explosive molecules may more easily be detected, once transferred to appropriate detecting devices.

Once an appropriate sample has been collected with the apparatus according to the present invention, means are provided herein for transporting the same to an explosives detector. Generally, whatever means are provided for transporting the sample to an explosives detector, heating of the element should occur. By heating the element, the collected sample is vaporized so that the same may be transported to the detector. In the specific embodiment of a sampling apparatus according to the present invention, described below, transporting means include forced pure gas means. Specifically, once molecules on the surface of the collector element are vaporized, a flow of pure gas then transports the same without significant loss to a detector. Suitable pure gases for transporting the explosives molecules include hydrogen, helium, nitrogen, or the like. It should be readily recognized that other transportation means may also be utilized to deliver a collected sample to an explosives detector, so that any specific embodiments outlined herein should not be deemed unduly limiting to the present invention.

The novel the sampler apparatus of the present invention are designed so that a collected sample may be transported to a suitable detector. As such, the use of the sampler apparatus of the present invention in conjunction with an explosives detector to which samples are delivered is encompassed by the present invention.

To aid further those desiring to practice the present invention, the following exemplary embodiment of an explosive sampler apparatus according to the present invention is provided. The specific embodiment discussed is shown in FIGS. 1 and 2 herein. In this regard, it is noted that the components shown in FIG. 1 are as follows:

1. two way valve (open/closed);
2. oven;
3. two way valve for pure gas supply (open/close);
4. fast heater;
5. sampling tube or needle;
6. three way valve to which is attached a GC column and a vacuum line;
7. an ECD or IMS detector receiving the flow from the GC column;
8. gas chromatographic column for rapid separation of the explosive components from each other;

The pure gas supply, high voltage supply, associated electronics, vacuum pump, and other ancillary equipment are located in a case which is attached to the sampling head by an umbilical tube which carries the necessary supply lines.

The sampling head contains a cool (room temperature) front valve (1) which is attached to, but thermally insulated from, a nickel tube (10) in an oven (2). Inside the nickel tube is a needlelike quartz, fused silica, or metal tube (5) which is attached to a second heated valve (6). One port of (6) is connected to a GC column which terminates in an ECD or IMS; the second port is attached to a vacuum pump in the ancillary box. There is a third valve (3) which supplies pure gas to the nickel tube in the proper part of the cycle. The oven (2) also contains a slide mechanism which allows the sampling tube to exit through (1) when it is open in order to collect a sample. Subsequently, the tube is returned into the nickel tube to be heated to release the sample into the GC.

The sequence of operation events for the sample head is:

1) Before starting, 1 is closed to the exterior, and the sampling tube is heated by 2, the pure gas being introduced through 3 into the nickel tubing in oven 2; Valve 6 is connected to the GC;
2) At the starting impulse, 1 switches to open, the sampling tube is pushed through 1 by the sliding mechanism;
3) 6 switches to the vacuum pump, and 3 switches closed;
4) After sample collection, 3 switches to pure gas flow, and 6 switches to the column;
5) The slide mechanism returns to its original position, bringing the sampling tube back inside the nickel tube in 2; Valve 1 closes;
6) The sample is desorbed from the sampling tube with extra heat from 4, separated into its individual components by the GC, and each component is detected by the ECD or IMS;

7) The time duration between desorption and detection of each component is the data necessary to determine if an explosives component is present.

When the quartz tube is first pushed to the outside air, it is hot from the oven. However, it cools very quickly because of its extremely low mass. The explosives vapor molecules adsorb on the sample tube and are desorbed inside the system by heating with 4 and 2. The GC separates the sample in a short time (<3 sec.) into its individual components, and the ECD detects any explosive species. Before obtaining the next sample, the quartz sampling tube is heating in the nickel tube, and any remaining air and contaminants are swept through the column and away.

The collection and subsequent detection of the sample would be the same for monitoring personnel, packages, car interiors, room interiors, various furniture/articles in a room or vehicle, etc., and is as follows.

In order to collect a meaningful sample of explosives vapor, if any is present, the instrument must be placed in or passed through the vapor cloud. This means that the user must be aware of any wind patterns in the sampling vicinity, and must sample downwind. The instrument is turned on, and when the quartz sampling tube is exposed, a sample is taken of the air in close proximity to the surface being tested. The unit may be "scanned", i.e., passed along the surface, or may simply be placed in the volume of air to be tested. Since the process is rapid, many samples can be obtained and tested in a short time.

Quartz, fused silica, glass, or other siliceous material, or appropriate metal tubes can be used as sampler elements. Whatever material is chosen, it is important that it allows for preconcentration of a sample to occur (i.e., it allows for the adsorption of explosives molecules from a large volume of air and later allows the molecules to be desorbed into a small volume of air). Such preconcentration effectively allows one to increase the volume of explosives vapor/volume air, thus making the detection of explosives molecules much easier.

The explosives samplers of the present invention are preferably hand-held units, which can most preferably be operated easily in real time by one operator. Moreover, the operation of such samplers should preferably be simple so that non-technical persons can operate the instrument properly, efficiently, and easily.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed:

1. An explosives detection system comprising:

a closed housing having inner and outer walls defining a protected heated environment;

an open-ended cylindrical tube disposed within said housing, said tube having a first end attached to said inner wall of said housing and a second end projecting inwardly within said housing, said housing defining a first opening therethrough in axial alignment with said cylindrical tube;

a first valve attached to said housing defining an open passageway in axial alignment with said first opening and said cylindrical tube when said first valve is in an open position;

a second valve having a tubular extension nested with and slidably engaging said cylindrical tube so as to be movable along the axis thereof, said tubular extension and said cylindrical tube defining a generally cylindrical volume of variable length, said second valve having an inlet port in axial alignment with said cylindrical volume and first and second outlet ports which selectively communicate through said second valve with said inlet port;

a sampling tube attached at one end to the inlet port of said second valve disposed coaxially within said cylindrical volume, the other end of said sampling tube being extendable through said first opening and said open passageway in said first valve to a point beyond said first valve and housing and into the environment being sampled during a sample collection operation to maximize collection of sample materials thereon, said sampling tube being fully retractable within said cylindrical volume during a sample detection operation;

means for selectively heating said sampling tube to vaporize all sample materials collected thereon;

means for selectively supplying pure gas to said cylindrical volume during detection and pre-collection operations;

vacuum means in communication with said first outlet port of said second valve means;

a gas chromatography column located within said housing in communication with said second outlet port of said second valve means, and detector means located within said housing in communication with said gas chromatography column to identify the constituents of said sample.

2. The explosives detection system of claim 1, wherein said sampling tube comprises:

a siliceous material or a metal having an affinity for explosives molecules.

3. The explosives detection system of claim 2, wherein said siliceous material or metal comprises:

quartz, fused silicon, glass, gold, nickel or stainless steel.

* * * * *